United States Patent
Koshti et al.

(10) Patent No.: US 11,311,474 B2
(45) Date of Patent: Apr. 26, 2022

(54) TRANSPARENT PERSONAL CLEANSING COMPOSITIONS

(71) Applicant: GALAXY SURFACTANT, Navi Mumbai (IN)

(72) Inventors: Nirmal Koshti, New Jersey, NJ (US); Ananda Shamrao Hodage, Dombivali (IN); Pooja Vaidya Kshirsagar, Nagpur (IN); Bhagyesh Jagannath Sawant, Kalyan (IN); Pravinkumar Devkatte, Nanded (IN); Sukanya Talukdar, Thane (IN)

(73) Assignee: GALAXY SURFACTANTS LTD., Navi Mumbai (IN)

(*) Notice: Subject to any disclaimer, the term of this patent is extended or adjusted under 35 U.S.C. 154(b) by 248 days.

(21) Appl. No.: 16/814,498

(22) Filed: Mar. 10, 2020

(65) Prior Publication Data
US 2020/0289401 A1   Sep. 17, 2020

(30) Foreign Application Priority Data
Mar. 11, 2019 (IN) .............................. 201921009419

(51) Int. Cl.
| A61K 8/00 | (2006.01) |
| A61K 8/92 | (2006.01) |
| A61K 8/34 | (2006.01) |
| A61K 8/37 | (2006.01) |
| A61K 8/67 | (2006.01) |
| A61Q 5/02 | (2006.01) |
| A61K 8/44 | (2006.01) |

(Continued)

(52) U.S. Cl.
CPC .............. *A61K 8/922* (2013.01); *A61K 8/046* (2013.01); *A61K 8/342* (2013.01); *A61K 8/375* (2013.01); *A61K 8/44* (2013.01); *A61K 8/442* (2013.01); *A61K 8/678* (2013.01); *A61Q 5/02* (2013.01); *A61Q 19/10* (2013.01)

(58) Field of Classification Search
CPC ......... A61K 8/922; A61K 8/046; A61K 8/375
See application file for complete search history.

(56) References Cited

U.S. PATENT DOCUMENTS

| 6,723,311 B1* | 4/2004 | Seipel ...................... A61K 8/31 424/70.11 |
| 8,383,090 B2 | 2/2013 | Ariotto et al. |
| 10,092,492 B2* | 10/2018 | Terrisse ................. A61K 8/604 |

(Continued)

OTHER PUBLICATIONS

Belanger, et al., "Aquatic Risk assessment of alcohol ethoxylates in North America and Europe", Ecotoxicology and Environmental Safety, 64, pp. 85-99. (2006).

(Continued)

*Primary Examiner* — Necholus Ogden, Jr.
(74) *Attorney, Agent, or Firm* — Kramer & Amado, P.C.

(57) ABSTRACT

A transparent personal cleansing composition for skin and hair care comprises non-ionic and anionic surfactants with hydrophobe of lauryl group in the vegetable oil which exhibit enhanced foaming and lather capacity in comparison to the marketed products. The personal care composition of the present invention avoids harsh or toxic anionic ether sulphate type surfactants, eco-toxic non-ionic fatty alcohol ethoxylates, fatty alkanol amides and a host of other ingredients that are not derived from renewable sources.

19 Claims, 3 Drawing Sheets

(51) Int. Cl.
*A61K 8/04* (2006.01)
*A61Q 19/10* (2006.01)

(56) References Cited

U.S. PATENT DOCUMENTS

| | | | |
|---|---|---|---|
| 2004/0258647 A1* | 12/2004 | Ruppert | A61K 8/922 424/70.16 |
| 2007/0161524 A1* | 7/2007 | Counradi | A61K 8/463 510/130 |
| 2016/0361242 A1* | 12/2016 | Durtschi | A61K 8/88 |
| 2019/0083370 A1* | 3/2019 | Wankhade | A61Q 19/10 |
| 2019/0117546 A1* | 4/2019 | Wei | A61K 8/922 |
| 2020/0170894 A1* | 6/2020 | Park | A61K 8/26 |

OTHER PUBLICATIONS

Eadsforth, et al., "Monitoring of Environmental fingerprints of alcohol ethoxylates in Europe and Canada", Ecotoxicology and Environmental Safety, 64, pp. 14-29. (2006).

Jurado, et al., "Acute toxicity and relationship between metabolites and ecotoxicity during the biodegradation process of non-ionic surfactants: fatty-alcohol ethoxylates, nonylphenol polyethoxylate and alkylpolyglucosides", Water Science & Technology—WST, 59.12, pp. 2351-2358. (2009).

Loden, et al., "Contact Dermatitis & Allergy Irritation potential of bath and shower oils before and after use: a double-blind randomized study", British Journal of Dermatology, 150, pp. 1142-1147. (2004).

Sivak, et al., "Environmental and Human Health Aspects of Commercially Important Surfactants", Solution Behavior of Surfactants—Theoretical and Applied Aspects, Springer, Boston, vol. 1, pp. 161-188. (1982).

Johnson, et al. "Safety Assessment of Alkyl Glyceryl Ethers as Used in Cosmetics", International Journal of Toxicology 32, Supplement 3, 17 pages. (Dec. 19, 2011).

Environment Canada, "Canadian Envrionment Protection Act, 1999, Federal Environmnetal Quality Guidelines, Alcohol Ethoxylates", 20 pages. (Downloaded Jun. 11, 2020).

* cited by examiner

TRANSPARENT PERSONAL CLEANSING COMPOSITIONS

FIELD OF INVENTION

The present invention relates to transparent personal cleansing compositions for skin and hair care comprising non-ionic and anionic surfactants with hydrophobe of lauryl group in the vegetable oil which exhibits high foaming property, is non-irritating and is highly sustainable with high 'natural origin' index. The composition of the present invention is mild, free of toxic and hazardous surfactants and other chemicals which can cause damage to the environment. Particularly, the composition of the present invention is waterless vegetable oil-based composition.

BACKGROUND AND PRIOR ART

The product category of 'Shower oils' is one of the technologies of 'mild cleansing'. The oil based formulations do not remove the water-soluble NMF (natural moisturizing factor) from corneocytes of stratum corneum (topmost layer of skin) which is responsible for skin's hydration. Also, oil based formulations do not disturb 'brick and mortar' arrangement of corneocytes and lipids of stratum corneum while cleansing skin of dirt, sebum and bacteria. The occlusive nature of oil-based cleansers helps in the overall maintenance of hydration of skin. Dry and sensitive skin as well as skin with dermatological conditions is prone to get easily sensitized and inflamed and hence 'oil based' mild cleansers are most suitable in maintenance of the hygiene.

According to Mintel Survey (2018), the category of oil based cleansers is led by Beiersdorf with its brands, Nivea and Eucerin. Other leading products in the market are Unilever's Dove, L'Occitane's Body Shower oil and Luxurious foaming oil No 7 by Boots.

'ApotheCARE Essentials in-shower oil' and 'Pure Sense shower cleansing oil' are interesting and innovative launches of 2018 (entries 6 & 7).

These all leading shower oils in the market (Table 1) contain MIPA laureth sulphate (CAS No 83016-76-6) as anionic oil-soluble surfactant that is based on ethoxylated fatty alcohol which is manufactured by sulphating (Sulphur trioxide or chlorosulphonic acid) and neutralizing by mono isopropanol amine (MIPA). The sulphation step of ethoxylated fatty alcohol always results in generation of suspected carcinogen 1,4-dioxane. Also, the harshness of fatty alcohol sulphates and/or ether sulphates on skin is well known and hence the emergence of the 'sulphate-free' aqueous personal cleansing products like body washes and shampoos. (For example, 'sulphate-free' shampoo by L'Oreal and 'sulphate-free' body wash by Unilever). U.S. Pat. No. 8,383,090 B2 explains this aspect of science pertaining to sulphate type of surfactants and their harshness on skin. The same patent also talks about the fatty alkanol amides that are often used to boost foam in shower oils and their implication for the generation of carcinogenic N-nitrosamines (Table 1).

Interestingly, Marie Loden et al. (British Journal of Dermatology, 150, 1142-47, 2004) compared shower oils containing MIPA laureth sulphate with shower oils without MIPA laureth sulphate (Table 2). Shower oils containing sulphate type of surfactants fared very badly compared to the ones without sulphates in terms of rate of TEWL (trans epidermal water loss) and cutaneous blood flow measurement by a laser Doppler flowmeter. A couple of 'sulphate-free' shower oils launched in 2018, for example, Apothe CARE Essentials in-shower oil and Pure Sense shower cleansing oil (entry no 6 and 7 of Table 1). These two shower oils employ TIPA (triisopropanol amine) lauroyl sarcosinate that is supposed to eliminate the disadvantage of MIPA laureth sulphate in shower oils.

However, it is pertinent to mention here that all 'sulphate-free' shower oils in the market suffer from several serious limitations and disadvantages. The major limitation is the extremely poor foam during bathing process. Luxurious foam/lather is much desired attribute by the consumer for a bathing/cleansing composition. The second biggest disadvantage suffered by 'sulphate-free' shower oils is that they contain lower mole fatty alcohol ethoxylates in significant

TABLE 1

| Sr. No. | Product Name | Company | Launched on | Ingredients |
| --- | --- | --- | --- | --- |
| 1 | L'Occitane Body Shower Oil | L'Occitane | December 2018 | TIPA-laureth sulfate, *Vitis vinifera* Seed Oil, Laureth-3, *Butyrospermum parkii*, Caprylic/Capric Triglyceride, Cocamide MEA, *Helianthus annuus* seed Oil, Tocopherol |
| 2 | Dove Nourishing Care Shower Oil | Unilever | August 2018 | *Helianthus annuus* oil, Laureth-3, MIPA-laureth Sulfate, Laureth-7 Citrate, parfum, *Argania spinosa* Kernel Oil, BHT, Cocamide MEA, Glycerin, Hydrogenated Palm Glycerides Citrate, Phenoxyethanol, Tocopherol |
| 3 | Eucerin pH 5 Shower Oil | Beiersdorf | Septempber 2018 | Glycine Soja Oil, Laureth-4, MIPA-laureth Sulfate, *Ricinus communis* seed oil, Tocopherol |
| 4 | Nivea Shower Oil | Beiersdorf | November 2018 | Glycine Soja Oil, Laureth-4, MIPA-laureth Sulfate, *Ricinus Communis* Seed Oil, Tocopherol |
| 5 | No. 7 Luxurious Foaming Shower Oil | Boots | December 2012 | Caprylic/Capric Triglyceride, Laureth-3, MIPA-laureth Sulfate, Laureth-7 Citrate, perfume (fragrance), *Vitis vinifera* Seed Oil, *Argania spinosa* Kernel Oil, Tocopherol |
| 6 | Apothe CARE Essentials In- shower oil | Unilever | March 2018 | *Helianthus annuus* seed oil, Laureth-3, TIPA-lauroyl sarcosinate, fragrance Phenoxyethanol, Cocamide MEA, Stearic Acid, BHT, *Rosa canina* fruit oil |
| 7 | Pure Sense | Marico | 2018 | Macadamia oil, almond oil, Coconut oil, TIPA lauroyl sarcosinate, Laureth -3 | percentages as part of the final compositions. The lower mole ethoxylates are known to be highly toxic to aquatic life. (1. Little, A. D. *Human Safety and Environmental Aspects of Major Surfactants*; A Report to The Soap and Detergent Association, New York, 1977. 2. Goyer, M. M.; Perwak, J. H.; Sivak, A.; Thayer, P. S.; Lithe, A. D. *Human Safety and Environmental Aspects of Major Surfactants* (Supplement); A report to: The Soap and Detergent Association, 1981. 3. Sivak, A.; Goyer, M.; Perwak, J.; Thayer, P. Environmental and Human Health Aspects of Commercially Important Surfactants. In *Solution Behavior of Surfactants Theoretical and Applied Apects*; Mittal, K. L.; Fendler, E. J., Eds.; Springer: Boston, 1982; Vol. 1; pp 161-188. 4. Talmage, S. S. *Environmental and Human Safety of Major Surfactants: Alcohol Ethoxylates and Alkylphenol Ethoxylates*, $1^{st}$ Ed.; Lewis Publishers: Boca Raton, 1994. 5. Eadsforth, C. V.; Sherren, A. J.; Selby, M. A.; Toy, R.; Eckhoff, W. S.; McAvoy, D. C.; Matthijs, E. Monitoring of environmental fingerprints of alcohol ethoxylates in Europe and Canada. *Ecotoxicol. Environ. Saf.* 2006, 64, 14-29. 6) Belanger, S. E.; Dorn, P. B.; Toy, R.; Boeije, G. Marshall, S. J.; Wind, T.; Compernolle, R. V.; Zeller, D. Aquatic risk assessment of alcohol ethoxylates in North America and Europe. *Ecotoxicol. Environ. Saf.* 2006, 64, 85-99. 7. Jurado, E.; Fernández-Serrano, M.; Núñez-Olea, J.; Luzón. G.; Lechuga, M. Acute toxicity and relationship between metabolites and ecotoxicity during the biodegradation process of non-ionic surfactants: fatty-alcohol ethoxylates, nonylphenol polyethoxylate and alkyl polyglucosides. *Water Sci. Technol.* 2009, 59, 2351-2358. 8) Sanderson, H.; Compernolle, R. V.; Dyer, S. D.; Price, B. B.; Nielsen, A. M.; Selby, M.; Ferrer, D.; Stanton, K. Occurrence and risk screening of alcohol ethoxylate surfactants in three U.S. river sediments associated with wastewater treatment plants. *Sci. Total Environ.* 2013, 463-464, 600-610. 9) *Canadian Environmental Protection Act,* 1999; Government of Canada. Federal Environmental Quality Guidelines. Alcohol Ethoxylates, 2013).

Lower mole ethoxylates of fatty alcohol are marine pollutants and are classified as hazardous chemicals and yet they are employed by all the leading products in the market (Table 1). It is to be noted that some of the 'sulphate-free' formulations of Table 2 also contain silicone derivatives and paraffin in addition to marine pollutant lower mole ethoxylates of fatty alcohol. Silicone derivatives and paraffin used are not derived from 'renewable sources' (Table 2, entries 1, 2, 3 & 4). Use of 'non-renewable' material is certainly a serious concern with respect to planet's ability to sustain.

In summary, one can see that the products in the market contain one or more undesired ingredients that are skin irritating and carcinogenic dioxane containing MIPA laureth sulphate, carcinogenic nitrosamine generating cocamide DEA, marine pollutant fatty alcohol ethoxylates, non-renewable raw materials like petrolatum or non-degradable polysiloxane derivatives. These shower oils are for personal cleansing (bathing) wherein the ingredients constituting shower oils go to the environment after bathing or washing. Hence, any ingredient which does not come from renewable source works against the principle of sustainability and is harmful to the planet in the long run.

TABLE 2

| | | | |
|---|---|---|---|
| 1 | Reckitt Benckiser/ Crookes Healthcare Ltd, UK | E45 Emollient Bath Oil | Paraffinum liquidum, Cetyl dimethicone, C12-13 Pareth-3. |
| 2 | ACO Hud AB, Sweden | ACO Shower & Bath Oil | Paraffinum liquidum, Trilaureth-4 phosphate. |
| 3 | ACO Hud AB, Sweden | ACO Intimate Wash Oil | Paraffinum liquidum, Canola, Oleth-5,. |
| 4 | Stiefel Laboratories Ireland Ltd, Ireland | Ceridal Bath Oil | Paraffinum liquidum, *Vitis vinifera*, Laureth-4, Sorbitan sesquioleate,. |
| 5 | Hermal Kurt Herrmann, Germany | Balneum Hermal Bath/Shower Oil for dry Skin | Soybean Oil, Laureth-4, Oleamide DEA,. |
| 6 | Sebapharma, Germany | Sebamed Shower Oil | *Persea gratissima*, Lecithin, MIPA-Laureth sulphate, Laureth-4, Poloxamer 101, Cocamide DEA, Lactic Acid. |
| 7 | Beiersdorf, Germany | Nivea Shower Oil | Glycine Soya, MIPA-Laureth sulphate, *Recinus communis*, Laureth-4, Cocamide DEA. |
| 8 | Beiersdorf, Germany | pH 5 Eucerin Shower oil | Glycine Soya, MIPA-Laureth sulphate, *Recinus communis*, Laureth-4, Cocamide DEA, Poloxamer 101, Panthenol, Lanolin alcohol, Bisabolol. |

The second drawback of current shower oils from the market is the lack of adequate foam and lather while bathing which is one of the most desired consumer attribute. Oil-based shower oils are not expected to foam like water-based shower gels or body washes. The current shower oils in the market are extremely low foaming therefore are not of consumers choice since it does not give them a complete bathing experience. The same can be seen from the consumer's feedback on the internet. (https://www.apothecare-essentials.com/us/en/body/products/in-shower-oil/the-restorer-in-shower-oil.html; https://healthybeautyme.com/best-body-wash-for-dry-skin/).

Hence there is a need in the art to create oil-based formulations that would be safe, non-irritating, sustainable and without compromising on the 'mild cleansing and foaming' performance. In other words the need can be expressed as oil-based formulations that would be 1) significantly better foaming (at least twice as much of current market products) and 2) with 'natural origin index' of minimum 80% as per ISO 16128-2 and without harsh, non-ecofriendly ingredients.

Objectives of the Invention

It is therefore the objective of the present invention is to provide waterless vegetable oil based personal cleansers with minimum 80% natural origin content as per ISO 16128-2.

The other objective of the present invention is to provide vegetable oil based cleansers for personal care without using 1) sulphates or sulphonate based anionic surfactants 2) ethylene oxide based anionic or non-ionic surfactants, 3) fatty alkanolamide 4) petrochemicals like paraffin (mineral oils), 5) toxic antimicrobial preservatives and other toxic ingredients that are being currently used.

Yet another objective of the present invention is to provide vegetable oil based cleanser with very low irritation potential coupled with the best performance with respect to TEWL (Trans Epidermal Water Loss) from the skin, moisturization and sensory attributes than the current oil based cleansers.

The other objective of the present invention is to provide a vegetable oil based cleanser composition which is stable at low temperature, does not separate into layers at 10-15° C. and which outperforms current compositions available in market in terms of consumer desired attribute of foam and lather.

SUMMARY OF THE INVENTION

In accordance with the above objectives, the present invention provides transparent personal cleansing compositions with minimum 80% natural origin content as per ISO 16128-2 and with minimum foam of 450 cc for a 5% solution in water of 150 ppm hardness as measured by Hart De George method, comprising of,
  a) 40 to 60% by weight of one or more vegetable oils,
  b) 5 to 20% by weight of lauryl alcohol,
  c) 7 to 15% by weight of glyceryl mono laurate and/or glyceryl lauryl ether,
  d) 25 to 30% by weight of triisopropanol amine lauroyl sarcosinate and
  e) optionally, further pharmaceutical or cosmetic auxiliaries, additives and active ingredients.

In an aspect, the personal cleansing composition of the present invention is free of water.

In another aspect, the personal cleansing composition of the present invention is stable at low temperature and does not separate into layers at 10-15° C.

In yet another aspect, the composition of the present invention are useful for cleansing skin and hair.

The above described features and advantages of the present disclosures will be appreciated and understood by those skilled in the art from the detailed description and the claims.

DETAILED DESCRIPTION OF THE INVENTION

The term or phrase such as 'shower oils', 'vegetable oil based cleansing composition', 'transparent personal cleansing composition' mean and refer to the composition described in the entire specification.

Figure 1:
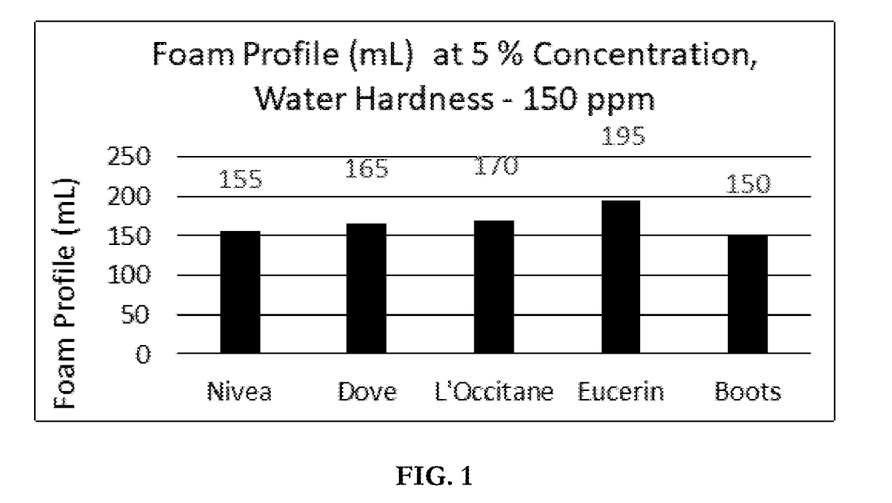
FIG. 1 depicts the Foam profile of marketed products such as Nivea, Dove, L'Occtaine, Eucerin and Boots at 5% concentration and water hardness of 150 ppm.

The shower oils available in the market (e.g., Dove, Nivea, Eucerin etc. of Table 1) shows that foam created from 5% solution using Hart De George method is around 200 cc (FIG. 1). Further, all market products of FIG. 1 contain MIPA laureth sulphate and fatty alcohol ethoxylates. Some of them are reported to have fatty alkanol amides as well. The shower oils of Apothe CARE Essentials and Pure Sense shower oils contain TIPA lauroyl sarcosinate and lauryl alcohol ethoxylate. These two products though solve the problem of avoiding harshness of 'sulphate-type' of anionic surfactant two basic problems still remain, i.e. a) low in-use foam (<200 cc) and b) use of aquatic pollutant, the lower mole fatty alcohol ethoxylates.

Surprisingly, the inventors of the present invention found that a particular combination of non-ionic and anionic surfactants with hydrophobe of lauryl group in the vegetable oil based cleansing composition can foam more than double the volume of market products.

In an embodiment, the present invention discloses transparent personal cleansing compositions with minimum 80% natural origin content and with minimum foam of 450 cc for a 5% solution in water of 150 ppm hardness as measured by Hart De George method, comprising of,
  a) 40 to 60% by weight of one or more vegetable oils,
  b) 5 to 20% by weight of lauryl alcohol,
  c) 7 to 15% by weight of glyceryl mono laurate and/or glyceryl lauryl ether,
  d) 25 to 30% by weight of triisopropanol amine lauroyl sarcosinate and
  e) optionally, further pharmaceutical or cosmetic auxiliaries, additives and active ingredients.

The vegetable oils and lauryl alcohol of the composition constitute the oily part of the composition. The surfactant part of the composition comprises of four parts, 1) vegetable oil, 2) lauryl alcohol 3) anionic surfactant, TIPA lauroyl sarcosinate and 4) non-ionic surfactants, lauryl derivatives of glycerin, namely, glyceryl mono laurate or glyceryl lauryl either alone or together.

In another embodiment, the transparent personal cleansing composition of the present invention is free of water.

In yet another embodiment, the personal cleansing composition of the present invention is stable at low temperature and does not separate into layers at 10-15° C.

With sulphate-surfactant or without sulphate-surfactant, the market products gave very low foam of <200 cc (FIGS. 1 and 2, the ingredient list is given for all market products in Table 1 and Table 2 in prior art section) whereas Examples of 3 (FIG. 2) to 13 demonstrate the oil based compositions based on a combination of lauryl based both anionic and nonionic surfactants with vegetable oils to foam more than the double volume of market products. The recorded foam volumes are upwards of 400 cc, in most cases it is 450 to 600 cc.

In another embodiment, the transparent personal cleansing composition of the present invention provides foam volume in the range of 450 to 600 cc for a 5% solution in water of 150 ppm hardness as measured by Hart De George method.

Vegetable Oils:

The vegetable oils (40 to 60% by weight) of the composition are derived from any part of the plant. The examples of such oil include but is not limited to coconut oil, soybean oil, sunflower oil, palm kernel oil, olive oil, jojoba oil, neem oil, macadamia oil, argan oil, almond oil, grape seed oil, soap nut oil, Tea tree oil, wheat germ oil, rice germ oil, rosemary oil, castor oil, rapeseed oil, Tung oil, mustard oil, peanut oil and Shae butter. Many of the oils are used for nutrient value and these find their usefulness for their ester content and as well other phytochemicals including vitamins and lecithin etc. Some vegetable oils like Rosemary oil is known for hair care benefit including hair growth. Similarly, coconut oil is extremely popular in hair care in Asia and Africa for its overall benefits. Oil like Rosemary is also used for its fragrance. Tea tree oil (native of Australia) is also reported to possess anti-dandruff (anti-fungal) activity and is selected for hair oil cleansers. Castor oil (native of India) is used for its anti-inflammatory properties in shower oil. Its hair care benefits are reported for follicle growth and overall shine. Neem oil (native of India) is pressed from fruits and seeds and is used for its antiseptic properties which are mainly derived from the triterpenoid, Azadirachtin. Neem oil's antidandruff properties also makes it useful for hair oil cleansing formulations (Example 7). Argan oil (native of Morocco), though an edible oil like sunflower or soya bean oil, is very popular for its benefits for personal care application. Jojoba oil (native of Arizona, USA) is not a triglyceride (largely mono esters of long chain fatty acids and fatty alcohol) is also useful ingredient for skin care as well as for hair care and can be a part of oil based formulations of the present invention.

Soybean Oil is extremely high in lecithin and vitamins (B, E and K) which makes it an effective moisturizing agent. It is a vitamin-rich emollient that absorbs well into the skin. Soybean Oil has a nourishing, softening and moisturizing effect on skin, hair and nails. It replenishes skin lipids and restores suppleness and flexibility. As a skin care ingredient, soy is reported to diminish wrinkles, reverse sun damage and even tighten sagging skin. It is an excellent emollient. Sunflower seed oil is also rich in calcium, iron, magnesium, zinc and vitamins A, K, and E and it is effectively used against inflammation of skin as emollient. Beta carotene is converted into its Vitamin A and gives protection from the damage due to sunrays and UV induced free radicals. Oils containing linoleic acid (omega-6) are in general useful for treating eczema and acne. Another popular personal care vegetable oil is Shae butter (origin Africa) that is mainly triglyceride of long chain fatty acids. Macadamia nut/kernel (Australia) oil contains the highest percentage of monosaturated fats along with vitamin A1, B1, B2, niacin and essential elements such as calcium, iron, phosphorus, magnesium and potassium. Avocado oil (native of Mexico) is another oil that finds its utility in cosmetics. Any of these vegetable oils, alone or in combination, is suitable for the composition of the present invention.

Lauryl Alcohol:

Lauryl alcohol (CAS no 112-53-8) is one of the four components (5 to 20% by weight) of the compositions of the present invention which is derived from vegetable oils like coconut or palm kernel oil that have significant percentage of lauryl triglycerides. Lauryl alcohol used in the compositions of the present invention is 95 to 100% pure. It can have other alcohols C8, C10 or C14 alcohol, all put together can be 5% max. Pure lauryl alcohol gives the best performance with respect to foam and commercially pure lauryl alcohol is available. Alcohols with higher alkyl (higher than C12) chain reduce the foam and raise the freezing point (induce solidification at higher temperature) of the final composition. Alkyl chain lower than C12 too exhibit lowering of foam of final composition and have strong characteristic odor. Example 14 is with 5% lauryl alcohol and Example 9 is with 20% lauryl alcohol Anionic Surfactant:

Anionic surfactant for vegetable oil based compositions of the present invention is selected from triisopropanol amine (TIPA) lauroyl sarcosinate (CAS No 2077159-86-3, Formula 1). It is present in amount of 25 to 30% by weight of the total oil based composition.

Formula 1

Figure 2:
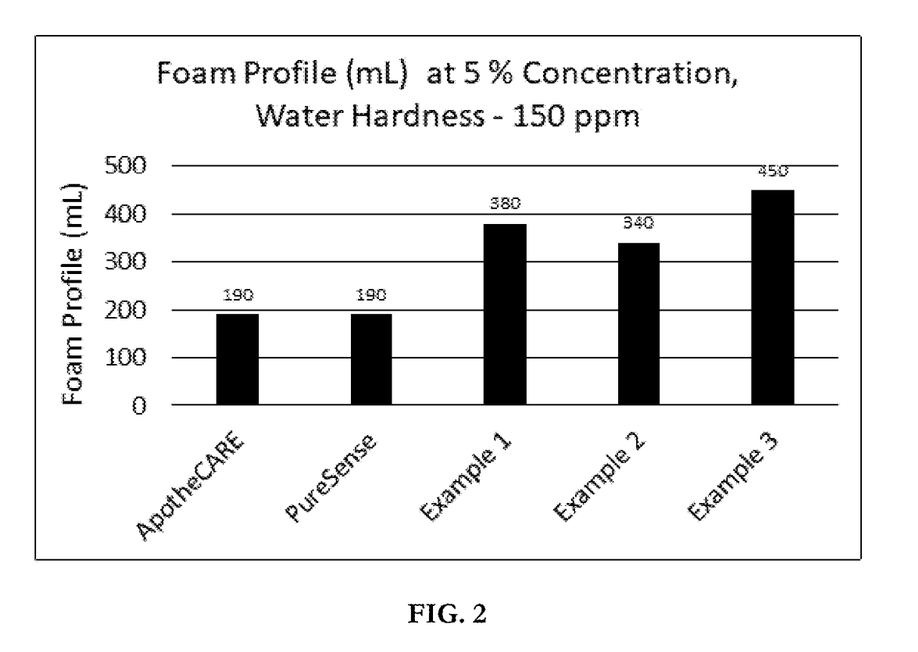
FIG. 2 depicts the comparative Foam profile of the composition (example 1, 2 and 3) of the present invention to the foam profile of the marketed products Apothe Care and Pure Sense at 5% concentration and water hardness of 150 ppm.

This surfactant has been used and as mentioned in the prior art two commercial launches of shower oil have been reported in 2018. Both products (FIG. 1, Apothe CARE Essentials and PureSense) employ TIPA lauroyl sarcosinate and lower mole fatty alcohol ethoxylate. Shower oil formulation of comparative Example 2 shows that TIPA lauroyl sarcosinate at 25% along with laureth-3 showed foam of 340 ccs (FIG. 2). However, surprisingly when laureth-3 (marine pollutant) was replaced by a combination of glyceryl mono laurate and lauryl alcohol as provided by the present composition the foam performance dramatically improved (450 cc, Example 3, FIG. 2). This surprising finding not only displaced toxic substance but also improved 'natural origin content' of the final composition as per ISO 16128-2 from 75% (Example 2) to 85%. (Example 3). In fact the foam analysis of all examples (3 to 13) of the present invention showed foam 450 cc or upwards of 450 cc. Another oil soluble sarcosinate variant is of MIPA cocoyl sarcosinate (EC number 943-406-1, CAS number is not available). According to literature MIPA cocoyl sarcosinate (one of the components of Sebumol S 1000 by Zschimmer and Schwarz, Germany) has been used with fatty alcohol and glyceryl mono laurate in comparative Example 1, however, the foam generation has been on the lower side (380 cc) by Hart De George method (Experimental section). The combination of TIPA lauroyl sarcosinate with nonionic surfactants with C12 carbon chain and fatty alcohol with C12 carbon chain resulted in foam generation of 450 cc to 600 cc. No product in market has foaming generation that is anywhere close to the oil-based cleansing compositions claimed in the present invention as depicted by several examples in Experimental section (3 to 13).

Nonionic Surfactants:

Non-ionic surfactants employed in the compositions of the present invention are selected from glyceryl mono laurate (CAS No 27215-38-9, Formula 2) and/or glyceryl lauryl ether (CAS No 1561-07-5, Formula 3). These non-ionic surfactants are used in an amount of 7 to 15% by weight of the total compositions. It can be noted that the anionic surfactant used in the composition of the present invention is based on C12 alkyl chain as well as the C12 chain of nonionic surfactants and the fatty alcohol.

Glyceryl lauryl ether as well as glyceryl mono laurate are made from vegetable oil derived ingredients, namely, glycerin, fatty acid and fatty alcohol. Glyceryl mono laurate is a food emulsifier and glyceryl lauryl ether belongs to class of alkyl glyceryl ethers that are reported to be safe surfactants. (Cosmetic Ingredient Review: safety assessment of alkyl glyceryl ethers as used in cosmetics, Dec. 19, 2011)

Formula 2

Formula 3

Glyceryl lauryl ether is used in examples 6, 11 and 13. The other examples disclosed comprise glyceryl mono laurate. Example 13 discloses the combination of both nonionic surfactants. Use of these two non-ionic surfactants based on C12 alkyl chain along with C12 based TIPA lauroyl sarcosinate not only significantly improved the foam profiles of the oil based compositions of the present invention but also displaced the toxic fatty alcohol ethoxylates that are present in all current commercial shower oil products (Table 1). The non-ionic surfactants of the present invention also replaced the nitrosamine (carcinogen) causing alkanol amides that are pretty common in current shower oils in the market (Table 1). It is to be noted that despite these toxic foam boosters like fatty alkanol amides and fatty alcohol ethoxylates, the marketed products do not show much consumer-desired attribute of 'foam' for a rinse off cleansing product. Glycerin and lauric acid are abundantly available in nature in the form of vegetable oils. Similarly some of the other polyhydric alcohols can be exploited for creating lauric esters. For example, monolauryl ester of naturally derived 1,3-propane diol can work in the similar way of glycerin derivatives of lauric group however, glycerin is by far the most cost-effective natural polyhydric alcohol available.

Auxiliary Ingredients:

The auxiliary ingredients for personal care cleansing compositions of the present invention are selected from all oil-soluble actives or benefit ingredients like Vitamins A and E, derma purifiers like capryloyl glycine and undecylenoyl glycine, oil soluble anti-aging molecules mainly, lipidated tri or tetra and penta peptides, polyglyceryl-fatty acid esters, Palmitoyl Pentapeptide-3 (Matrixyl) and 4, anti-inflammatory palmitoyl tetrapeptide-7, essential oils, oil-soluble fragrances. Substances like DL Panthenol, though water soluble, can be dissolved at small percentage in the compositions described here.

Performance Evaluation:

Shower oils of the current invention ((Example 3) have been compared with shower oils with fatty alcohol ethoxylates (Example 2) keeping the amount of anionic surfactant (TIPA lauroyl sarcosinate) and amount of vegetable oil (soybean oil) the same. Both shower oil formulations have been compared for 1) Foam generation
2) Moisturization (corneometry)
3) Rate of trans epidermal loss of water (TEWL) using Tewameter
4) Sensory attributes by human panel of experts Foam Generation:

From the data presented in FIG. 2 it can be seen that the Example 3 is significantly higher foaming than Example 2. Foam evaluation protocol is given in the experimental section.

Figure 3:
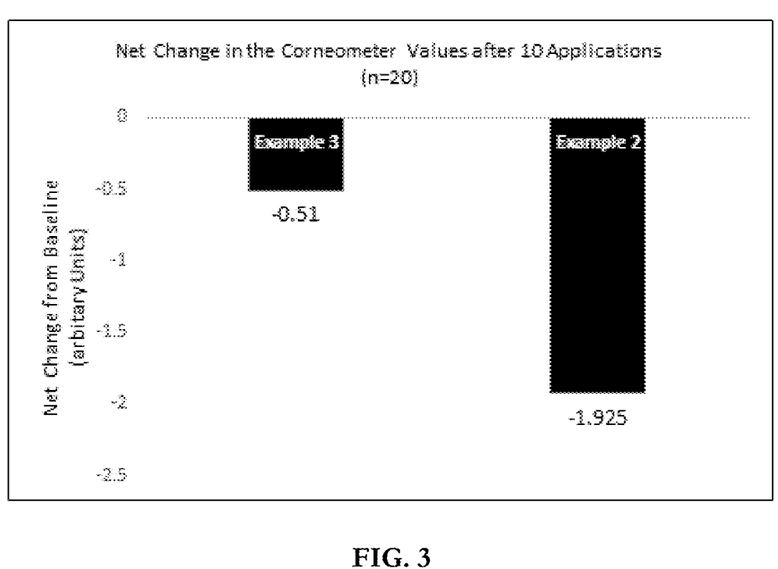
FIG. 3 depicts the net change in the corneometer values of composition (example 2 and example 3) of the present invention.

Moisturization:

Formulation of Example 3 has been found to be superior to formulation of Example 2 in terms of moisturization of skin (FIG. 3). This could be attributed to damaging effect (lipid solubilizer) of fatty alcohol ethoxylates (Example 2) on lipids of stratum corneum against skin beneficial effect (refatting agent) of glyceryl mono laurate of example 3. Evaluation details are given in the Experimental section.

Figure 4:
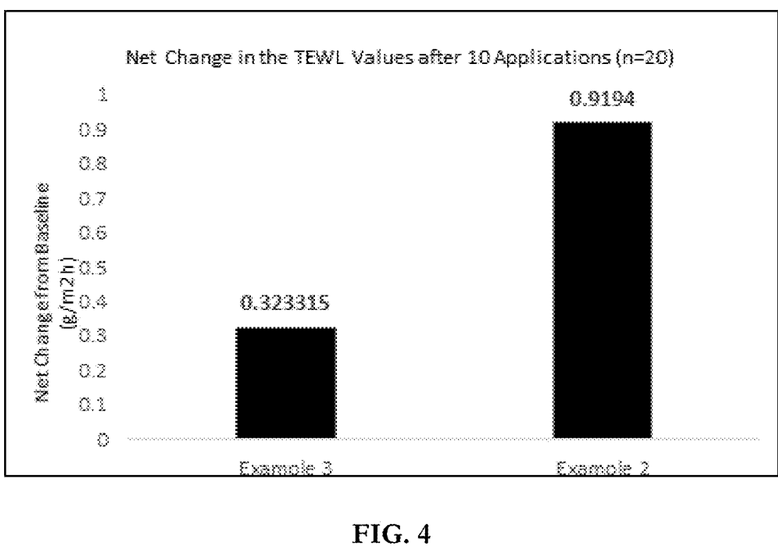
FIG. 4 depicts the net change in the TEWL values of composition (example 2 and example 3) of the present invention.

Rate of Trans Epidermal Water Loss:

For the same reason cited above, the Shower oil composition of Example 3 showed superior results in terms of rate of water loss from skin when compared with shower oil of Example 2. FIG. 7 shows significant change in TEWL in case of Example 3 compared to Example 2. Lipid solubilization properties of fatty alcohol ethoxylates seem to damage the 'brick and mortar' structure of stratum corneum and thus resulting in higher rate of water loss as shown in FIG. 4.

Figure 5:
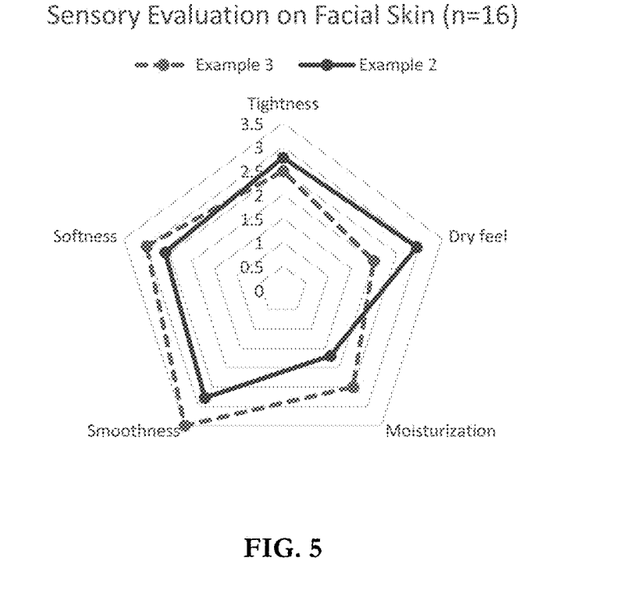
FIG. 5 depicts the sensory evaluation on Facial skin of the present composition.

Sensory Attributes Evaluation:

In terms of sensory attributes evaluation, Shower oil of Example 3 showed superior sensory attributes against shower oil of Example 2 when compared with respect to five parameter, smoothness, moist feel, tightness, soft feel and dry feel (FIG. 5). Evaluation protocol is given in the Experimental section.

Example 3 represents the basic composition of the present invention with its four key components. It has been tested on human volunteers for the dermal irritation by 'Repeat Insult Patch Test' protocol (Shelanski method) and is found to be non-irritant. The composition of Example 3 is readily biodegradable as per OECD 301D. The Hair oil composition of Example 7 has been used on hair tresses. The hair oil of Example 7 is applied and left on hair for a couple of minutes and then rinsed off with water. The washed hair are dried and subjected to wet and dry combing using Dia-Stron tensile tester MTT175. The ease of combing reflected by reduction in combing force between hair treated with hair oil cleanser (Example 7) and regular shampooed hair shows the benefit of hair cleansing oil (Example 7) where hair are not damaged at all due to removal of natural lipids from hair strands that happens during the routine cleansing process with a shampoo.

Advantages:

Oil-based compositions of the present invention are unique since they do the adequate cleansing without damaging the skin. The vegetable oil based cleansers of the present invention are suitable for sensitive and irritated skin as well as diseased skin. These are useful for baby skin, adult skin as well as old people's skin. Oil based cleansers described herein are suitable for their dual role of hair cleansing and conditioning.

The vegetable oil based cleansers of the present invention do not use any of the toxic and non-sustainable ingredients, namely, 1,4-dioxane containing sulphate type of surfactants, PEGs, marine pollutant and hazardous fatty alcohol ethoxylates, nitrosoamine causing alkanol amides, petrochemicals like paraffin, silicone derivatives and toxic antimicrobials.

Oil based compositions of the current invention are readily biodegradable (OECD 301D).

Vegetable oil based compositions of this application are with high content of 'natural origin' (above 80%) as defined by the guidelines of ISO 16128-2 (2017) and with renewable carbon index of min 85%.

The waterless compositions of this invention are both 'sulphate-free' and 'fatty alcohol ethoxylate' free. This not only makes them sustainable but also improves overall performance. These compositions show significantly superior performance in terms of moisturization, trans epidermal water loss (dryness), sensory attributes and foam compared to all products from the market (FIG. 1 and FIG. 2).

In summary, the cleansing compositions of the present invention are green/sustainable as well as delivering superlative performance on any type of skin (normal or compromised) or any type of hair compared to any offering available in the market or reported in the literature. The cleansing compositions of the present invention avoid all toxic and non-sustainable ingredients and perform beautifully in terms of mild cleansing and hence can be suitable for baby care after adding some more vegetable oils like sunflower or sesame oil to the present composition.

EXPERIMENTAL

The present invention is now described by way of working on limiting illustrative examples. These examples are provided for illustrative purposes only and are not intended to limit the scope of invention as defined in the claims below.

General Procedure for the Preparation of Shower Oil Formulations (Example 1-14):

Surfactants (MIPA Cocoyl Sarcosinate, and/or TIPA Lauroyl Sarcosinate; and Glyceryl Monolaurate, and/or Glyceryl Lauryl Ether) mixture is warmed to melt and simply mixed with oil phase/rest of the ingredients under slow agitation to yield homogeneous transparent formulation in 15 to 30 mins.

Transparency of the Shower Oil formulations mentioned in the invention: The transparent nature of the Shower Oil formulations in experiments 1 to 13 is measured by Turbidimetry (HACH Model 2100P Portable TURBIDIMETER Lot L9023) which operates on the nephelometric principle of turbidity measurement. The instrument was calibrated using Hach Stable Cal Stabilized Fomazin primary standards available in 0.5, 20, 100 and 800 NTU sealed vials (Cat. No. 26594-10). The instrument can measure the turbidity in the range 0-1000 NTU with ±2% accuracy. Turbidity is measured as ratio of nephelometric signal (90°) scattered light to transmitted light with turbidity of deionized water being 0.1 NTU. Turbidity measurements were made with automatic range selection mode at 25° C.

Hart De George Method for Foam Evaluation:

Oil-based rinse-off compositions mentioned in Experiments from 1 to 13 and some of the market products of FIGS. 1 and 2 are tested for foam generation by the following procedure. Shower oil (5 g) is mixed with water (95 mL, hardness 150 ppm). The pH of the suspension is around 5.5 to 6.0. The whole suspension (100 mL) is then transferred to a kitchen blender and mixed at a speed of 20000 rpm for 60 sec. Foam generated is then collected in the 1000 mL measuring cylinder and the foam volume is measured.

Skin Moisturization by Oil-Based Formulations of the Present Application

The Skin moisturization property is evaluated by measuring the hydration levels by Corneometry (Capacitance methodology, Courage Khazaka Electronic, Koln—MPA 5). The measurement is based on capacitance measurement of a dielectric medium which is water. It measures the change in the dielectric constant due to skin surface hydration changing the capacitance of a precision capacitor. Each test site is marked (4×4 sq. cm) on the volar forearm. Baseline measurement is taken for Corneometer values (arbitrary value). Sample application is done as per standard protocol. Shower oil is applied for 15 seconds in circular movements on the test sites. The applied sites are rinsed thoroughly with tap water (approx. 37 Deg. C) for 15 seconds and dried with a soft towel. The procedure is repeated 10 times and the panel size used is 20.

Net change in the corneometer values from baseline are compared graphically as evident in the FIG. 3. Example 3 is significantly better than shower oil compared to Example 2.

Rate of Trans Epidermal Water Loss by Oil-Based Formulations of Present Application TEWA property has been evaluated by measuring the hydration levels by Diffusion methodology using TEWAmeter (Diffusion methodology, Courage—Khazaka Instrument Version—MPA 5)

Each test site is marked (4×4 sq. cm) on the volar forearm. Baseline measurement is taken for Tewameter values (arbitrary value). Shower oil is applied for 15 seconds in circular movements on test sites. The applied sites are rinsed thoroughly with tap water (approx. 37 Deg. C) for 15 seconds and dried with a soft towel. The procedure is repeated 10 times and the panel size used is 20.

Net change in the TEWL values from baseline are compared graphically as shown in FIG. 4 Example 3 is significantly better than shower oil compared to Example 2.

Percentage Natural Origin Content

ISO 16128-2 (2017) prescribes guidelines on technical definitions and criteria for natural and organic cosmetics ingredients. Based on these guidelines % natural origin content is calculated.

Renewable Carbon Index:

Renewable carbon index was calculated as per its technical definitions i.e. (Number of carbons from renewable source/total number of carbons)×100.

Example No 1: (Shower Oil 1)

Shower Oil Based on MIPA Cocoyl Sarcosinate and Soya Oil.

| Ingredients | % w/w |
| --- | --- |
| Soya Bean oil (soybean) | 50 |
| Lauryl alcohol | 18 |
| Glyceryl mono laurate | 7.0 |
| MIPA cocoyl sarcosinate | 25 |

Turbidity: 0.98 NTU, Foam: 380 cc, Freezing point: <20° C., Natural origin content as per ISO 16128-2: 88.25% and Renewable carbon index: 91.66%.

Example 2: (Shower Oil 2)

Shower Oil Based on TIPA Lauroyl Sarcosinate and Laureth-3 and Soya Oil.

| Ingredients | % w/w |
| --- | --- |
| Soya Bean oil | 50 |
| Laureth-3 | 25 |
| TIPA lauroyl sarcosinate | 25 |

Turbidity: 0.40 NTU, Foam: 340 cc, Freezing point: <15° C., Natural origin content as per ISO 16128-2: 74.5%; and Renewable carbon index: 79.16%.

Example 3: (Shower Oil 3)

Shower Oil Based on TIPA Lauroyl Sarcosinate, Glyceryl Mono Laurate, Lauryl Alcohol and Soya Bean Oil.

| Ingredients | % w/w |
| --- | --- |
| Soya Bean oil | 50 |
| Lauryl alcohol | 18 |
| Glyceryl mono laurate | 7.0 |
| TIPA lauroyl sarcosinate | 25 |

Turbidity: 0.86 NTU, Foam: 450 cc, Freezing point: <15° C., Natural origin content as per ISO 16128-2: 85% and Renewable carbon index: 87.5%.

Example 4

Preparation of Shower Oil Based on Soya Bean Oil.

| Ingredients | % w/w |
| --- | --- |
| Soya Bean oil | 50 |
| Lauryl alcohol | 15 |
| Glyceryl mono laurate | 7.0 |
| TIPA lauroyl sarcosinate | 25 |
| Capryloyl glycine | 1.0 |
| Vitamin E | 0.5 |
| DL-Panthenol | 0.5 |
| Fragrance | 1.0 |

Turbidity: 0.80 NTU, Foam: 450 cc, Freezing point: <15° C., Natural origin content as per ISO 16128-2: 84.63% and Renewable carbon index: 87.3%.

Example No 5

Preparation of Shower Oil Based on Sunflower Seed Oil.

| Ingredients | % w/w |
| --- | --- |
| Sunflower Seed oil | 50 |
| Lauryl alcohol | 15 |
| Glyceryl mono laurate | 7.0 |
| TIPA lauroyl sarcosinate | 25 |
| Undecylenoyl glycine | 1.0 |
| Vitamin E | 0.5 |
| DL-Panthenol | 0.5 |
| Fragrance | 1.0 |

Turbidity: 0.95 NTU, Foam: 530 cc, Freezing point <15° C., Natural origin content as per ISO 16128-2: 84.67% and Renewable carbon index: 87.32%

Example No 6

Preparation of Shower Oil Based on Soya Bean Oil.

| Ingredients | % w/w |
| --- | --- |
| Soya Bean oil | 50 |
| Lauryl alcohol | 18 |
| Glyceryl lauryl ether | 5 |
| TIPA lauroyl sarcosinate | 24 |
| Capryloyl glycine | 1 |
| Vitamin E | 0.5 |
| DL-Panthenol | 0.5 |
| Fragrance | 1 |

Turbidity: 0.98 NTU, Foam: 550 cc, Freezing point: <20° C., Natural origin content as per ISO 16128-2: 85.23% and Renewable carbon index: 87.8%.

Example No 7

Preparation of Cleansing Hair Oil Based on Coconut Oil and Soybean Oil.

| Ingredients | % w/w |
| --- | --- |
| Coconut oil | 30 |
| Soybean oil | 17 |
| Lauryl alcohol | 15 |
| Glyceryl mono laurate | 7.0 |
| TIPA lauroyl sarcosinate | 25 |
| Capryloyl glycine | 0.5 |
| Undecylenoyl glycine | 0.5 |
| Neem oil | 1.0 |
| Jojoba oil | 1.0 |
| Soap Nut oil | 1.0 |
| Vitamin E | 0.5 |
| DL-Panthenol | 0.5 |
| Fragrance | 1 |

Turbidity: 0.88 NTU, Foam: 480 cc, Freezing point: <20° C., Natural origin content as per ISO 16128-2: 84.67%; and Renewable carbon index: 87.32%

Example No 8

Preparation of Shower Oil Based on Sunflower Seed Oil, Olive Oil, Soya Bean Oil.

| Ingredients | % w/w |
| --- | --- |
| Sunflower Seed oil | 20 |
| Soya Bean oil | 20 |
| Olive oil | 10 |
| Lauryl alcohol | 15 |
| Glyceryl mono laurate | 7.0 |
| TIPA lauroyl sarcosinate | 25 |
| Capryloyl glycine | 0.5 |
| Undecylenoyl glycine | 0.5 |
| Vitamin E | 0.5 |
| DL-Panthenol | 0.5 |
| Fragrance | 1 |

Turbidity: 0.98 NTU, Foam: 460 cc, Freezing point: <15° C., Natural origin content as per ISO 16128-2: 84.67%; and Renewable carbon index: 87.32%.

Example No 9

Preparation of Shower Oil Based on Sunflower Seed Oil, Soya Bean Oil.

| Ingredients | % w/w |
|---|---|
| Sunflower Seed oil | 20 |
| Soya Bean oil | 20 |
| Lauryl alcohol | 20 |
| Glyceryl mono laurate | 13 |
| TIPA lauroyl sarcosinate | 25 |
| Capryloyl glycine | 0.5 |
| Vitamin E | 0.5 |
| Fragrance | 1.0 |

Turbidity: 0.83 NTU, Foam: 460 cc, Freezing point: <20° C., Natural origin content as per ISO 16128-2: 84.82%; and Renewable carbon index: 87.4%.

Example No 10

Preparation of Shower Oil Based on Sunflower Seed Oil, Soya Bean Oil.

| Ingredients | % w/w |
|---|---|
| Sunflower Seed oil | 23 |
| Soya Bean oil | 23 |
| Lauryl alcohol | 15 |
| Glyceryl mono laurate | 8 |
| TIPA lauroyl sarcosinate | 30 |
| Vitamin E | 0.5 |
| Fragrance | 0.5 |

Turbidity: 0.82 NTU, Foam: 520 cc, Freezing point: <15° C., Natural origin content as per ISO 16128-2: 82.0%; and Renewable carbon index: 85.0%.

Example No 11

Preparation of Shower Oil Based on Sunflower Seed Oil, Soya Bean Oil.

| Ingredients | % w/w |
|---|---|
| Sunflower Seed oil | 23 |
| Soya Bean oil | 23 |
| Lauryl alcohol | 18 |
| Glyceryl lauryl ether | 5 |
| TIPA lauroyl sarcosinate | 30 |
| Vitamin E | 0.5 |
| Fragrance | 0.5 |

Turbidity: 0.97 NTU, Foam: 600 cc, Freezing point: <20° C., Natural origin content as per ISO 16128-2: 82.0%; and Renewable carbon index: 85.0%.

Example No 12

Preparation of Shower Oil Based on Sunflower Seed Oil, Soya Bean Oil.

| Ingredients | % w/w |
|---|---|
| Sunflower Seed oil | 30 |
| Soya Bean oil | 25 |
| Lauryl alcohol | 10 |
| Glyceryl mono laurate | 9 |
| TIPA lauroyl sarcosinate | 25 |
| Vitamin E | 0.5 |
| Fragrance | 0.5 |

Turbidity: 0.80 NTU, Foam: 580 cc, Freezing point: <15° C., Natural origin content as per ISO 16128-2: 85.0%; and Renewable carbon index: 87.5%.

Example No 13

Preparation of Shower Oil Based on Sunflower Seed Oil, Soya Bean Oil

| Ingredients | % w/w |
|---|---|
| Sunflower Seed oil | 30 |
| Soya Bean oil | 25 |
| Lauryl alcohol | 10 |
| Glyceryl lauryl ether | 4.5 |
| Glyceryl mono laurate | 4.5 |
| TIPA lauroyl sarcosinate | 25 |
| Vitamin E | 0.5 |
| Fragrance | 0.5 |

Turbidity: 0.90 NTU, Foam: 580 cc and Freezing point: <15° C., Natural origin content as per ISO 16128-2: 85.0%; and Renewable carbon index: 87.5%.

Example No 14

Preparation of Shower Oil Based on Sunflower Seed Oil

| Ingredients | % w/w |
|---|---|
| Sunflower Seed oil | 50 |
| Lauryl alcohol | 5 |
| Glyceryl mono laurate | 6.5 |
| TIPA lauroyl sarcosinate | 25 |
| Polyglyceryl -4 Oleate | 13 |
| Fragrance | 0.5 |

Turbidity: 0.90 NTU, Foam: 550 cc and Freezing point: <15° C., Natural origin content as per ISO 16128-2: 85.0%, and Renewable carbon index: 87.5%.

We claim:

1. A transparent personal cleansing composition, comprising;
   a) 40 to 60% by weight of one or more vegetable oils,
   b) 5 to 20% by weight of lauryl alcohol,
   c) 7 to 15% by weight of glyceryl mono laurate and/or glyceryl lauryl ether,
   d) 25 to 30% by weight triisopropanol amine lauroyl sarcosinate.

2. The transparent personal cleansing composition according to claim 1, wherein the transparent personal cleansing composition comprises at least 80% natural origin content, as defined by ISO 16128-2.

3. The transparent personal cleansing composition according to claim 1, wherein the transparent personal cleansing composition is configured to generate a foam volume of at least 450 cc upon mixing 100 mL of a suspension of 5 g of the transparent personal cleansing composition in 95 mL water at a speed of 20,000 rpm for 60 sec.

4. The transparent personal cleansing composition according to claim 3, wherein the water has a hardness of 150 ppm.

5. The transparent personal cleansing composition according to claim 1, further comprising at least one pharmaceutical or cosmetic auxiliary, additive, or active ingredient.

6. The transparent personal cleansing composition according to claim 1, wherein the vegetable oil is selected from the group consisting of coconut oil, soybean oil, sunflower oil, palm kernel oil, olive oil, jojoba oil, neem oil, macadamia oil, argan oil, almond oil, avocado oil, grapeseed oil, soap nut oil, tea tree oil, wheat germ oil, rice germ oil, rosemary oil, castor oil, rapeseed oil, tung oil, mustard oil, peanut oil, shae butter, and combinations thereof.

7. The transparent personal cleansing composition according to claim 1, wherein the vegetable oil is selected from the group consisting of coconut oil, soybean oil, sunflower oil, palm kernel oil, olive oil, and combinations thereof.

8. The transparent personal cleansing composition according to claim 1, wherein the transparent personal cleansing composition is used as a skin care formulation.

9. The transparent personal cleansing composition according to claim 1, wherein the transparent personal cleansing composition is used as a hair care formulation.

10. The transparent personal cleansing compositions according to claim 1, wherein the vegetable oil comprises coconut oil.

11. The transparent personal cleansing composition according to claim 9, wherein the vegetable oil comprises coconut oil.

12. The transparent personal cleansing compositions according to claim 1, wherein the transparent personal cleansing composition is free of water.

13. The transparent personal cleansing composition according to claim 12, wherein the transparent personal cleansing composition comprises at least 80% natural origin content, as defined by ISO 16128-2.

14. The transparent personal cleansing composition according to claim 12, wherein the transparent personal cleansing composition is configured to generate a foam volume of at least 450 cc upon mixing 100 mL of a suspension of 5 g of the transparent personal cleansing composition in 95 mL water at a speed of 20,000 rpm for 60 sec.

15. The transparent personal cleansing composition according to claim 12, wherein the vegetable oil is selected from the group consisting of coconut oil, soybean oil, sunflower oil, palm kernel oil, olive oil, jojoba oil, neem oil, macadamia oil, argan oil, almond oil, avocado oil, grapeseed oil, soap nut oil, tea tree oil, wheat germ oil, rice germ oil, rosemary oil, castor oil, rapeseed oil, tung oil, mustard oil, peanut oil, shae butter, and combinations thereof.

16. The transparent personal cleansing composition according to claim 12, wherein the transparent personal cleansing composition is used as a skin care formulation.

17. The transparent personal cleansing composition according to claim 12, wherein the transparent personal cleansing composition is used as a hair care formulation.

18. The transparent personal cleansing compositions according to claim 12, wherein the vegetable oil comprises coconut oil.

19. The transparent personal cleansing compositions according to claim 17, wherein the vegetable oil comprises coconut oil.

* * * * *